(12) United States Patent
Yang et al.

(10) Patent No.: US 8,594,809 B2
(45) Date of Patent: Nov. 26, 2013

(54) PASSIVE FIXATION MEDICAL ELECTRICAL LEAD

(75) Inventors: Zhongping Yang, Woodbury, MN (US); Amy Elizabeth Thompson, Coon Rapids, MN (US); Paulus G. Adams, Munstergeleen (NL); Koen Michels, Maastricht (NL)

(73) Assignee: Medtronic, Inc., Minneapolis, MN (US)

( * ) Notice: Subject to any disclaimer, the term of this patent is extended or adjusted under 35 U.S.C. 154(b) by 571 days.

(21) Appl. No.: 12/414,384

(22) Filed: Mar. 30, 2009

(65) Prior Publication Data
US 2009/0270962 A1 Oct. 29, 2009

Related U.S. Application Data

(60) Provisional application No. 61/047,837, filed on Apr. 25, 2008.

(51) Int. Cl.
*A61N 1/18* (2006.01)

(52) U.S. Cl.
USPC .......................................... 607/126

(58) Field of Classification Search
USPC ................... 607/116–117, 126, 129–131
See application file for complete search history.

(56) References Cited

U.S. PATENT DOCUMENTS

| | | |
|---|---|---|
| 4,282,886 A | 8/1981 | King |
| 4,541,440 A * | 9/1985 | Parsonnet ..................... 607/132 |
| 4,768,523 A | 9/1988 | Cahalan et al. |
| 5,044,374 A | 9/1991 | Lindemans et al. |
| 5,052,392 A | 10/1991 | Schullmeyer et al. |
| 5,476,500 A | 12/1995 | Fain et al. |
| 5,693,081 A | 12/1997 | Fain et al. |
| 5,897,585 A | 4/1999 | Williams |
| 6,123,723 A * | 9/2000 | Konya et al. ................. 623/1.11 |
| 6,159,531 A | 12/2000 | Dang et al. |
| 6,463,335 B1 * | 10/2002 | Munch et al. ................. 607/129 |
| 6,718,212 B2 | 4/2004 | Parry et al. |
| 7,085,606 B2 | 8/2006 | Flach et al. |
| 7,099,718 B1 | 8/2006 | Thacker et al. |
| 2004/0199237 A1 * | 10/2004 | Mills et al. ..................... 607/152 |
| 2009/0170124 A1 * | 7/2009 | Campbell ........................ 435/7.2 |

FOREIGN PATENT DOCUMENTS

WO WO 2006/105161 A2 10/2006

OTHER PUBLICATIONS (PCT/US2009/040638) PCT Notification of Transmittal of the International Search Report and the Written Opinion of the International Searching Authority, Jun. 7, 2009.

* cited by examiner

*Primary Examiner* — Amanda Patton
(74) *Attorney, Agent, or Firm* — Carol F. Barry (57) ABSTRACT

An implantable passive fixation lead is disclosed. The passive fixation lead comprises an elongate lead body having at least one elongate conductive element. The lead body includes a proximal end and a distal end. A support member has a first surface and a second surface. The second surface is coupled to the distal end of the lead body. A linking material is coupled to the first surface of the support member. A bioadhesive material is coupled to the linking material. A removable cover is placed over the bioadhesive material.

12 Claims, 9 Drawing Sheets

Table 1 - Chemical compounds used to form linking bioreactive material

| Chemical Name | Chemical Structure |
|---|---|
| (3-aminopropyl) trimethoxysilane (APTS) | $\text{CH}_3\text{O}-\underset{\underset{\text{OCH}_3}{|}}{\overset{\overset{\text{OCH}_3}{|}}{\text{Si}}}-\text{CH}_2\text{CH}_2\text{CH}_2\text{NH}_2$ |
| Epichlorohydrin (EPC) |  |
| 6-arm PEG - succinimidyl succinate (star-NHS) |  |
| Dextran (DEX) |  |
| polyacrylic acid | $\text{H}_2\text{C}=\text{CH}-\overset{\overset{\text{O}}{\|}}{\text{C}}-\text{OH}$ |

Fig. 10

PASSIVE FIXATION MEDICAL ELECTRICAL LEAD

CROSS-REFERENCE TO RELATED APPLICATIONS

This application claims the benefit of U.S. Provisional Application No. 61/047,837, filed on Apr. 25, 2008. The disclosure of the above application is incorporated herein by reference.

TECHNICAL FIELD

The present disclosure relates generally to implantable medical leads, and, more particularly, to passive fixation medical electrical leads.

BACKGROUND

The human anatomy includes many types of tissues that can either voluntarily or involuntarily, perform certain functions. After disease, injury, or natural defects, certain tissues may no longer operate within general anatomical norms. For example, after disease, injury, time, or combinations thereof, the heart muscle may begin to experience certain failures or deficiencies. Certain failures or deficiencies can be corrected or treated with implantable medical devices (IMDs), such as implantable pacemakers, implantable cardioverter defibrillator (ICD) devices, cardiac resynchronization therapy defibrillator devices, or combinations thereof.

IMDs detect and deliver therapy for a variety of medical conditions in patients. IMDs include implantable pulse generators (IPGs) or implantable cardioverter-defibrillators (ICDs) that deliver electrical stimuli to tissue of a patient. ICDs typically comprise, inter alia, a control module, a capacitor, and a battery that are housed in a hermetically sealed container with a lead extending therefrom. It is generally known that the hermetically sealed container can be implanted in a selected portion of the anatomical structure, such as in a chest or abdominal wall, and the lead can be inserted through various venous portions so that the tip portion can be positioned at the selected position near or in the muscle group. When therapy is required by a patient, the control module signals the battery to charge the capacitor, which in turn discharges electrical stimuli to tissue of a patient via electrodes disposed on the lead, e.g., typically near the distal end of the lead. Typically, a medical electrical lead includes a flexible elongated body with one or more insulated elongated conductors. Each conductor electrically couples a sensing and/or a stimulation electrode of the lead to the control module through a connector module.

In order to deliver stimulation or to perform sensing functions, it is desirable for the distal end of the lead to substantially remain in its position, as originally implanted by a physician. To stay in position, the distal end of the lead can be configured to be actively or passively fixed to tissue of interest. Active fixation refers to a lead electrode placed inside of tissue whereas passive fixation occurs when the electrode is placed on or near the surface of tissue. Actively fixing a lead to tissue can entail twisting a helical coil, disposed at the distal end of the lead, into the tissue of a patient. Suturing the lead to tissue is another active fixation means. While actively fixing the distal end of the lead to tissue substantially ensures that the lead remains in place, the tissue can experience some inflammation. Additionally, in some cases, such as children, active fixation of a lead may be difficult due to the size of the heart. Passive fixation of a lead, developed as an alternative to actively fixing a lead to tissue, involves use of an adhesive on the lead's distal end that can be stuck to the tissue, thereby reducing or eliminating inflammation of the tissue. Cyanocrylate adhesive, disclosed in U.S. Pat. No. 4,282,886, has been used to passively connect a lead to tissue. Alternatively, hydrogel, as disclosed in U.S. Pat. No. 4,768,523, has also been used to passively adhere a lead to tissue. Adhesives are placed directly onto a pad located at the distal end of the lead. The pad is then placed onto the epicardium. These adhesives, placed directly onto the pad, may not be tightly coupled or bonded to the pad. It is desirable to develop implantable medical electrical leads with new adherable fixation mechanisms.

BRIEF DESCRIPTION OF THE DRAWINGS

The following drawings are illustrative of particular embodiments of the present invention and therefore do not limit the scope of the invention. The drawings are not to scale (unless so stated) and are intended for use in conjunction with the explanations in the following detailed description. Embodiments of the present invention will hereinafter be described in conjunction with the appended drawings, wherein like numerals denote like elements.

DETAILED DESCRIPTION

The following description is merely exemplary in nature and is not intended to limit the present disclosure, application, or uses. The devices described herein include an exemplary number of leads, etc. One will understand that the components, including number and kind, may be varied without altering the scope of the disclosure. Also, devices according to various embodiments may be used in any appropriate diagnostic or treatment procedure, including a cardiac procedure. Leads disclosed herein are typically chronically implanted in a patient.

One or more embodiments relate to an implantable passive fixation lead. The lead comprises an elongate lead body and a support member disposed at the distal end of the lead body. The support member is configured to be passively fixated to tissue of a patient through the use of a bioreactive adhesion layer. A bioreactive adhesion layer, formed over the support member, comprises a linking material and adhesive material. The linking material is placed over, and, covalently bonds to the surface of the support member. A bioadhesive material is then placed over the linking material. The bioadhesive material covalently bonds onto the linking material. A removable cover is then placed over the bioadhesive material. The bioreactive adhesion layer ensures that an adhesive is secured in place.

Figure 1:
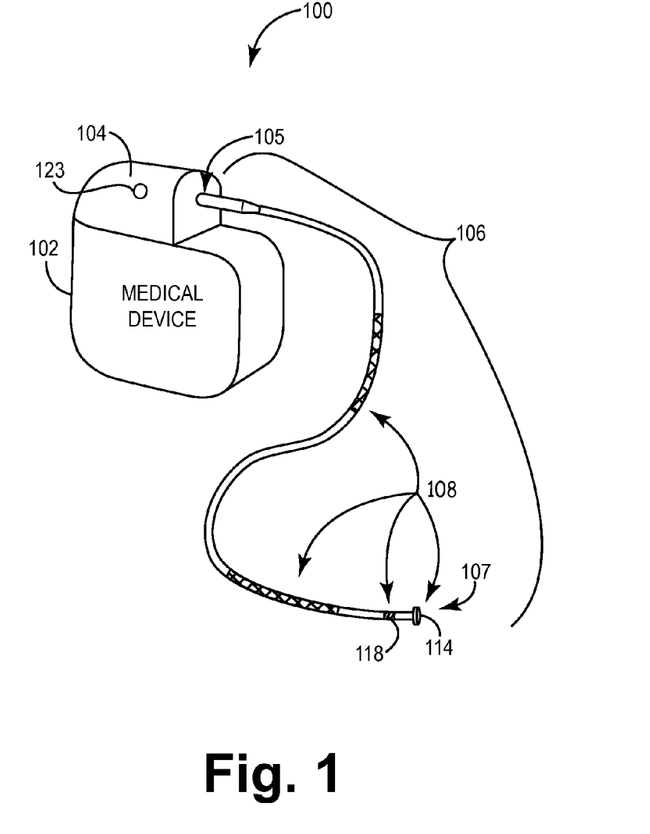
FIG. 1 is a conceptual schematic view of an implantable medical device in which a medical electrical lead extends therefrom.

FIG. 1 depicts a medical device system 100. A medical device system 100 includes a medical device housing 102 having a connector module 104 (e.g. international standard (IS)-1, defibrillation (DF)-1, IS-4 etc.) that electrically couples various internal electrical components housed in medical device housing 102 to a proximal end 105 of a medical electrical lead 106. A medical device system 100 may comprise any of a wide variety of medical devices that include one or more medical lead(s) 106 and circuitry coupled to the medical electrical lead(s) 106. As shown, lead 106 exemplifies an endocardial lead; however, it is to be appreciated that the disclosure herein also applies to epicardial leads. An exemplary medical device system 100 can take the form of an implantable cardiac pacemaker, an implantable cardioverter, an implantable defibrillator, an implantable cardiac pacemaker-cardioverter-defibrillator (PCD), a neurostimulator, a tissue and/or muscle stimulator. IMDs are implanted in a patient in an appropriate location. Exemplary IMDs are commercially available as including one generally known to those skilled in the art, such as the Medtronic CONCERTO™, SENSIA™, VIRTUOSO™, RESTORE™, RESTORE ULTRA™, sold by Medtronic, Inc. of Minnesota. Aspects of the disclosure can be used with many types and brands of IMDs. Medical device system 100 may deliver, for example, pacing, cardioversion or defibrillation pulses to a patient via electrodes 108 disposed on distal end 107 of one or more lead(s) 106. Specifically, lead 106 may position one or more electrodes 108 with respect to various cardiac locations so that medical device system 100 can deliver electrical stimuli to the appropriate locations. Support member 114 is used to secure the distal end 107 to tissue of a patient.

Lead 106 is an endocardial lead; however, as previously stated, the disclosure also applies to epicardial leads, as depicted and described relative to FIGS. 3, 4, 6A-8. Exemplary endocardial leads that can employ passive fixation mechanisms, as described herein, include CapSure® sold by Medtronic, Inc. of Minnesota. Endocardial leads are attached to the endocardium, the innermost layer of tissue that lines the chambers of the heart. The endocardium underlies the much more voluminous myocardium.

Figure 2:
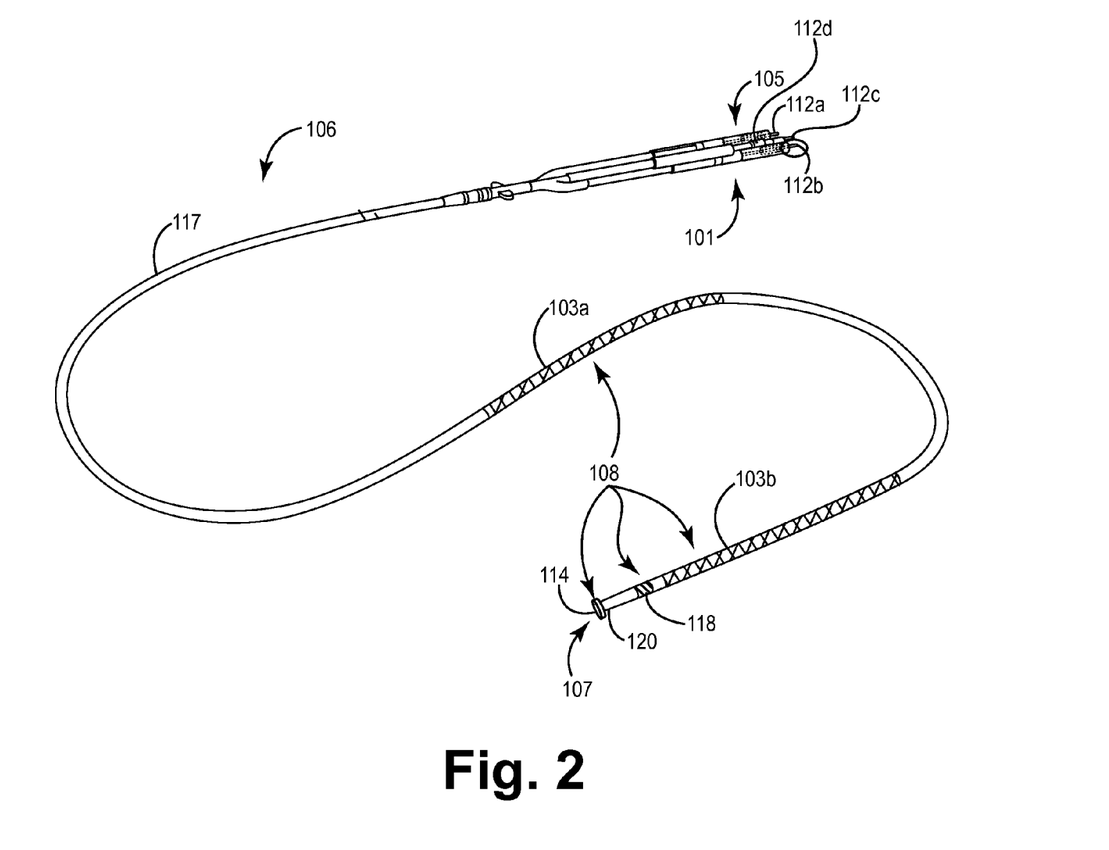
FIG. 2 is a schematic view of a medical electrical lead.

Lead 106 includes an elongated lead body 117 and a polymeric support member 114 for passively fixating the distal end 107 of the lead 106 to tissue of a patient. Each of these elements are described below. The elongated lead body 117 extends from a proximal end 105 to a distal end 107. Lead body 117 can include one or more connectors 101, and one or more jacketed elongated conductive elements 112a-d. A jacket (also referred to as a layer, longitudinal element, coating) extends along and longitudinally around the conductive elements 112a-d and serves to insulate one or more conductive elements 112a-d. Connector module 104 can include connectors 123, such as set screws, that electrically and mechanically connect conductive elements 112a-d to ports (not shown) of connector module 104. Conductive element 112c (also referred to as a "conductor coil," torque coil", "distal tip conductor") can extend to the distal end 107 and can optionally be coupled to a retractable and/or extendable tip. One or more conductive elements 112a,b serve as, or are connected to, defibrillation coils 103a,b that deliver electrical stimuli, when necessary, to tissue of a patient. Lead 106 can also include a conductive element 112d that extends from the proximal end 105 to ring electrode 118 while another conductive element 112c extends from proximal end 105 to tip electrode 120.

Electrically conductive elements 112a-d can include coils, wires, coil wound around a filament, cables, conductors or other suitable members. Conductive elements 112a-d can comprise platinum, platinum alloys, titanium, titanium alloys, tantalum, tantalum alloys, cobalt alloys (e.g. MP35N, a nickel-cobalt alloy etc.), copper alloys, silver alloys, gold, silver, stainless steel, magnesium-nickel alloys, palladium, palladium alloys or other suitable materials. Electrically conductive element 112a-d is covered, or substantially covered, longitudinally with a jacket (also referred to as a layer, a longitudinal element, a longitudinal member, a coating, a tubular element, a tube or a cylindrical element). Typically, the outer surface of electrodes 108 such as the ring electrode 118, the tip electrode 120, and the defibrillation coils 103a,b are exposed or not covered by a jacket or layer so that electrodes 108 can sense and/or deliver electrical stimuli to tissue of a patient. Support member 114 (also referred to as a pad or disk) is used to passively couple the distal end 107 of lead 106 to tissue, as described in greater detail relative to FIGS. 3, 4, and 6A-8.

Figure 3:
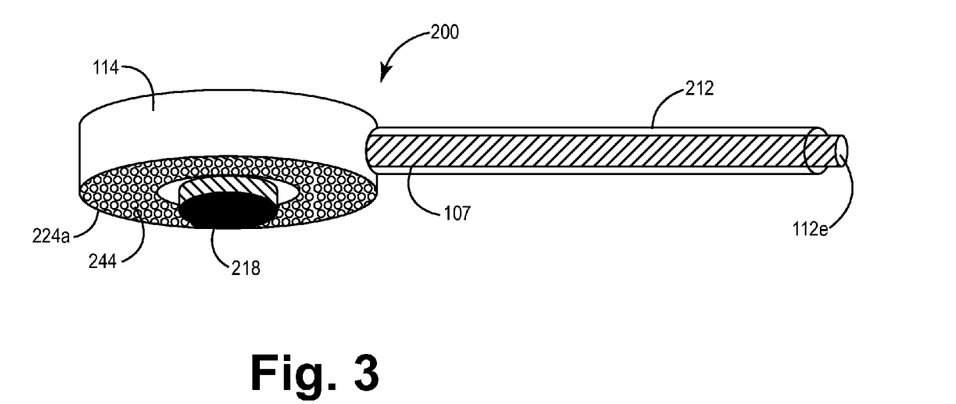
FIG. 3 is a schematic, partial cross-sectional view of a medical electrical lead.
Figure 4:
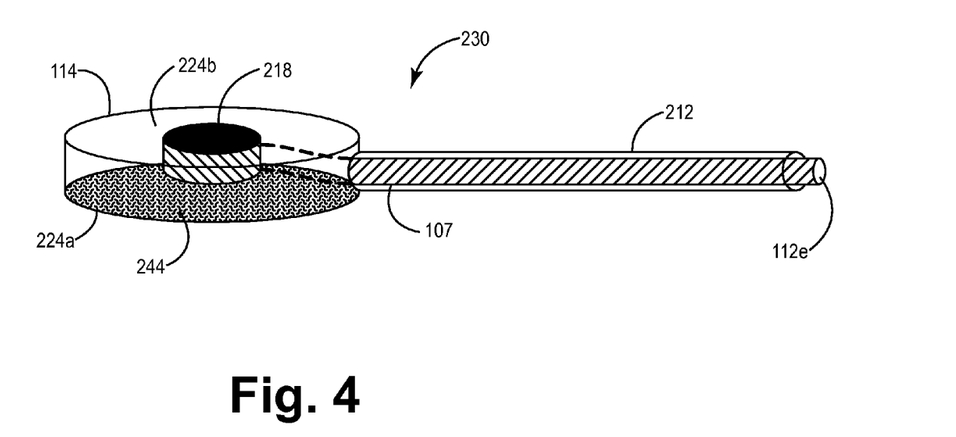
FIG. 4 is a schematic, partial cross-sectional view of a medical electrical lead.

Medical electrical lead 200, 230 depicted in FIGS. 3-4 respectively, represent an epicardial lead. Lead 200 comprises, inter alia, a lead body 212 and a support member 114 coupled at a distal end 107 of lead body 212. Lead body 212 can comprise one or more elongated conductive elements 112e covered by one or more elongated insulative jackets. Electrically conductive element(s) 112e is the same or similar to at least one of conductive elements 112a-d. An electrode 218, coupled to or part of the conductive element, is proximate the support member 114. In some embodiments, conductive element 112e can be partially inserted in the support member 114 with an electrode coupled to conductive element 112e. Support member 114 includes first and second opposing surfaces 224a,b respectively, in which first surface 224a, in combination with a bioreactive adhesion layer 248 shown in FIG. 5E, can be attached to tissue of the patient.

Bioreactive adhesion layer 248 ensures that adhesive material remains in place and does not easily move, fall or easily contact an undesirable surface such as the surface of an electrode or non-targeted tissue. Bioreactive adhesion layer 248 comprises linking material 242 and bioreactive material 244 (also referred to as bioreactive adhesive) formed over or placed onto support member 114. One or more embodiments for forming bioreactive adhesion layer 248 is shown relative to FIGS. 5A-5F.

Figure 5A:
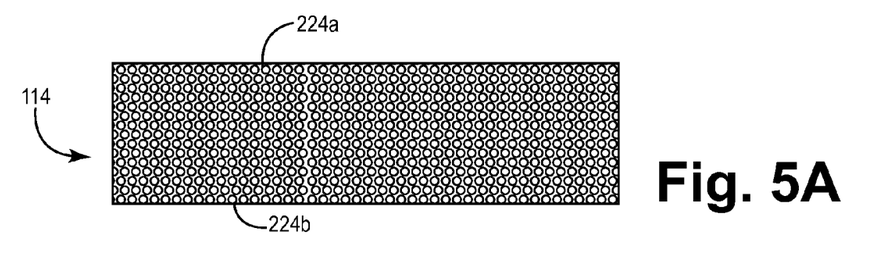
FIG. 5A is a schematic side elevation, cross-sectional view of a support member.
Figure 5B:
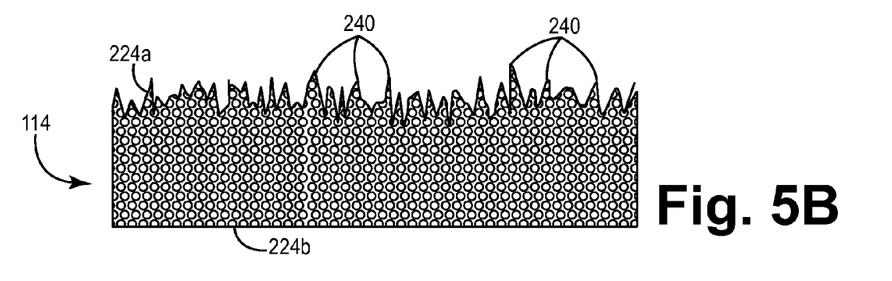
FIG. 5B is a schematic side elevation, cross-sectional view of a surface-treated-support member.

First surface 224a of support member 114, shown in FIG. 5A, can be substantially treated by increasing its original surface area (also referred to as appeared surface area or geometric surface area) through formation of height variations or peaks 240 as is shown in FIG. 5B. Increased surface area allows first surface area 224a to receive, and, covalently bond to, a linking material 242, as described below. First surface 224a can be roughened to include peaks 240. Surface roughening techniques can increase the surface area of polymeric support member 114 formed from polyurethane, silicone, or a combination thereof. The increased surface area can be referred to as a real surface area, which is the total surface area including peaks. Application of plasma over a surface of a support member 114 is one way to roughen a surface. For example, plasma, formed of argon/water (Ar/$H_2O$), can significantly increase the surface area of support member 114, which can be formed from a polymer such as polyurethane. In this embodiment, hydroxyl (OH) groups, disassociated from water, is added onto the polyurethane chain. The OH groups are then available to react and/or bond to polyurethane. Ethylene/nitrous oxide ($N_2O$) is yet another type of plasma that can be used to roughen the surface of support member 114. In this embodiment, oxygen can be added to the polyurethane. Alternatively, the surface of support member 114 can be washed in an ultrasonic water bath and then undergo a plasma treatment process. In addition to plasma treatment, molding, abrading, laser abrasion and other suitable techniques can be used to increase the surface area of support member 114. Alternatively, a surgical mesh, such as a Dacron mesh, can be attached to the first surface 224a in order to increase the surface area of the first surface 224a.

Figure 5C:
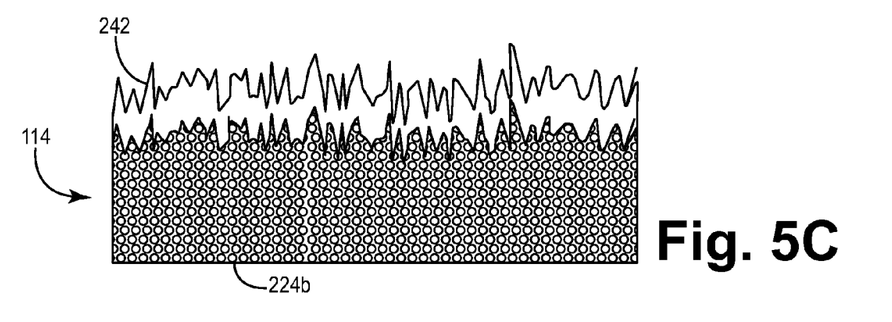
FIG. 5C is a schematic side elevation, cross-sectional view of a support member surface with linking material disposed thereon.
Figure 10:
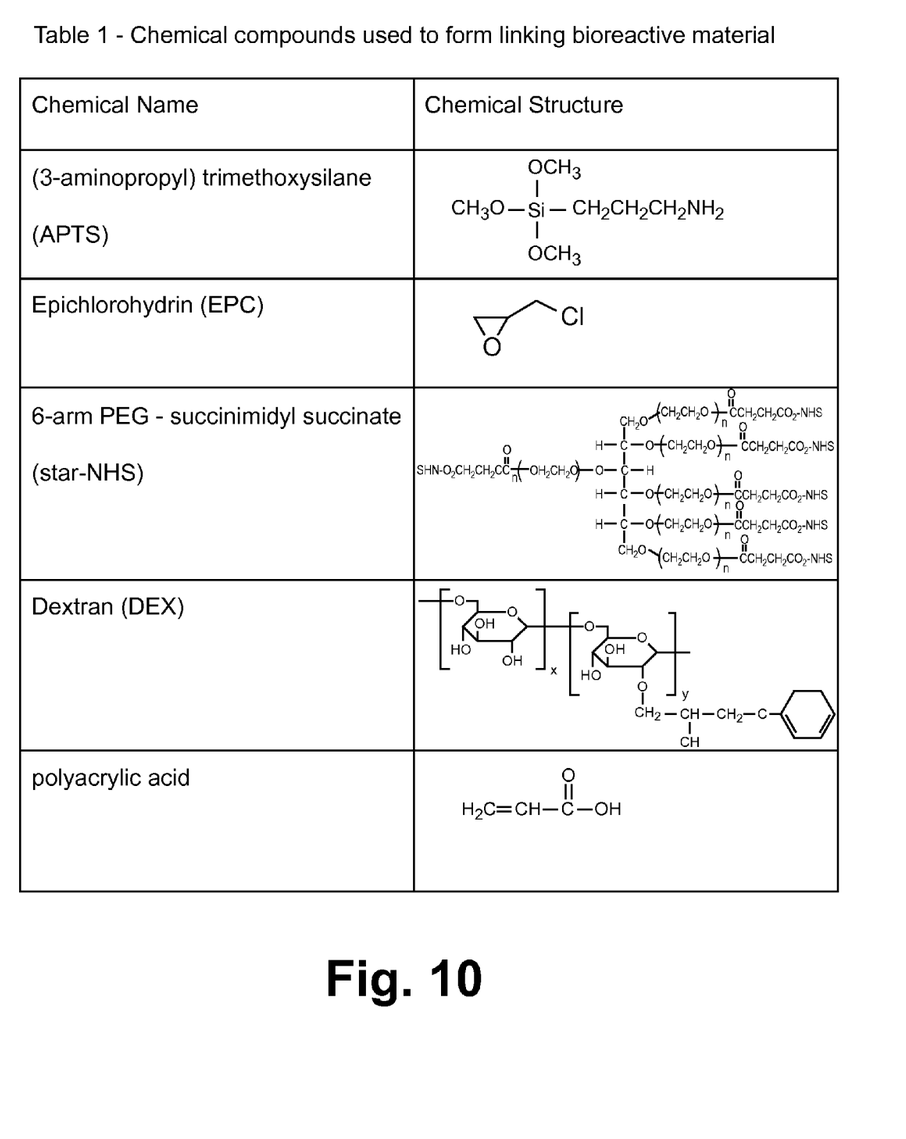
FIG. 10 depicts Table 1 which includes chemical structures of compounds used to form linking material.

After first surface 224a has had its surface area increased, support member 114 can be used as a substrate for receiving linking material 242, as shown in FIG. 5C. The linking material 242 is introduced over, or, attached to, a first surface 224a through coating, dipping painting and/or chemical vapor deposition. Linking material 242 is formed of at least one or more reactive compound(s) presented below in Table 1. Exemplary reactive compound(s) used to form linking material 242 can include (3-aminopropyl)trimethoxysilane (APTS) epichlorohydrin (EPC), (star PEG-succinimidyl succinate, dextran (DEX), and/or polyacrylic acid. All of these compounds are commercially available from Sigma-Aldrich located in St. Louis, Mo. Table 1, shown in FIG. 10, provides the chemical structure of the bioreactive compounds that can be used to form the linking material 242.

Figure 5D:
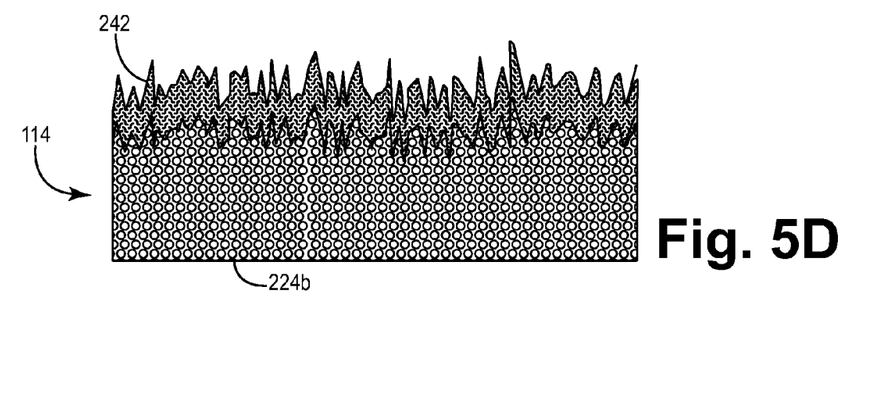
FIG. 5D is a schematic side elevation, cross-sectional view of linking material that has reacted with the support member.
Figure 5E:
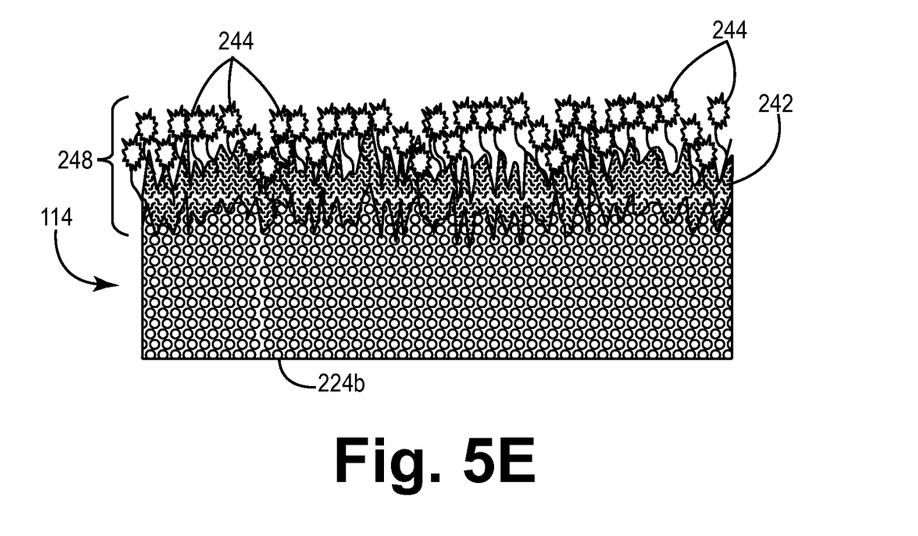
FIG. 5E is a schematic side elevation, cross-sectional view of a bioreactive adhesive material over the linking material.
Figure 5F:
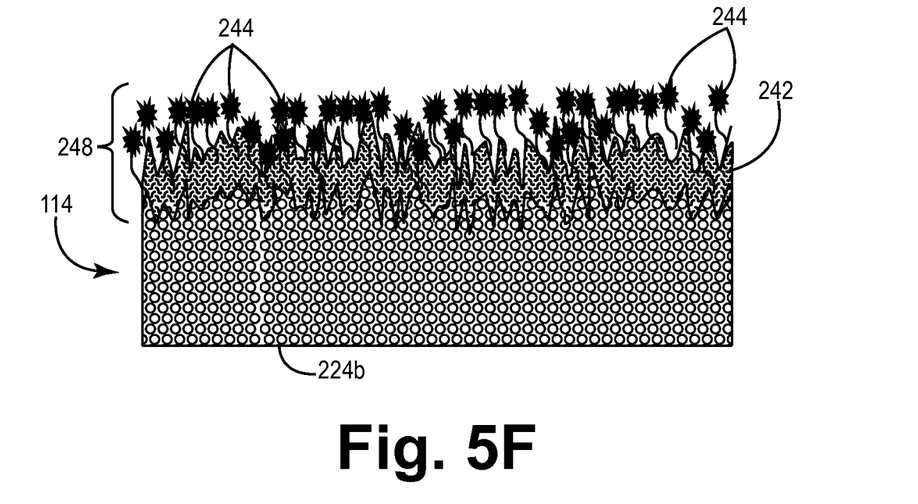
FIG. 5F is a schematic side elevation, cross-sectional view of a bioreactive adhesive material that reacted with the linking material.

In particular, the linking material 242 can chemically react and covalently bond with the first surface 224a of support member 114. Referring to FIG. 5D, linking material 242 links or securely bonds support member 114 to a bioadhesive material that is introduced over or placed directly onto linking material 242. In particular, bioadhesive material comprises at least one or more bioreactive layer 244. The edged-balls associated with bioreactive layer 244 merely schematically show the bioreactive layer 244 as including reactive components and does not represent an actual image of these components. FIG. 5F shows that the linking material 242 chemically reacts with a bioadhesive material, as shown by darkened bioreactive layer 244 for bioadhesion to tissue (not shown). Coating, painting, dipping, chemical vapor deposition are a few of the ways in which bioadhesive, that includes reactive compounds, can be placed onto linking material 242.

Bioreactive layer 244 forms a connection with biologic material such as the tissue. The interaction between the bioreactive layer 244 and tissue can cause a chemical reaction and/or a biological response such as an inflammatory response and/or immune response. The bioreactive layer 244 can makeup the bioadhesive material, which can then react with a tissue site in order to form a bond between the tissue site and the support member 114. The bioreactive layer 244 can contain a sulfide reactive group (e.g. mercapto-reactive group (—SH), disulfide (—S—S—) etc.), amino-reactive group such as aldehyde (—CHO), catechol, cyanide (—CN), succimide (—NHS) cyanoacrylates (e.g. n-butyl cyanoacrylate or 2-octyl cyanoacrylate) and/or N-hydroxysuccinimide. The chemical structures for catechol isomers is presented below:

catechol  resorcinol  hydroquinone

Table 2, presented below, summarizes exemplary substrates (i.e. material used to form support member 114) and bioadhesive molecule formulations that were grafted to polyurethane surfaces. It is to be appreciated that other suitable materials such as silicone or a combination thereof could be used, as previously discussed. Other types of reaction chemistries also exist. In the first formulation (PU-Dex-CHO), for example, polyurethane (PU) is used in support member 114, dextran (Dex) is the linking material, and -(aldehyde) (CHO) is the bioadhesive molecule. Other exemplary bioadhesive molecules include NH2, NH2-glutaraldehyde, polyacryl-NHS, NH2-star-NHS, Dextran-aldehyde, polyacryl-NHS with roughened surface, etc.

TABLE 2

Summary of exemplary substrates and reactions

| Formulation: | Rationale: |
| --- | --- |
| Polyurethane (PU)(pad)-Dex-(linker molecule)CHO(bioreactive compound) | Grafted dextran is converted to aldehyde functionality through oxidation. |
| PU-APTS-CHO | APTS introduces $NH_2$ groups on a surface. |
| PU-polyacrylate (polyAA) | PolyAA-grafted PU contains carboxylic acid groups and does not require the addition of dextran |
| PU-PolyAA-NHS | PolyAA further modified to —NHS functionality, which improves bioadhesion properties |
| PU-APTS-star-NHS | The star (branched) substrate allows for greater surface coverage with —NHS groups. |
| PU-EPC-Dex-NHS | EPC reacts with OH groups in polyurethane and acts as a linker molecule to bind dextran. |

Figure 6A:
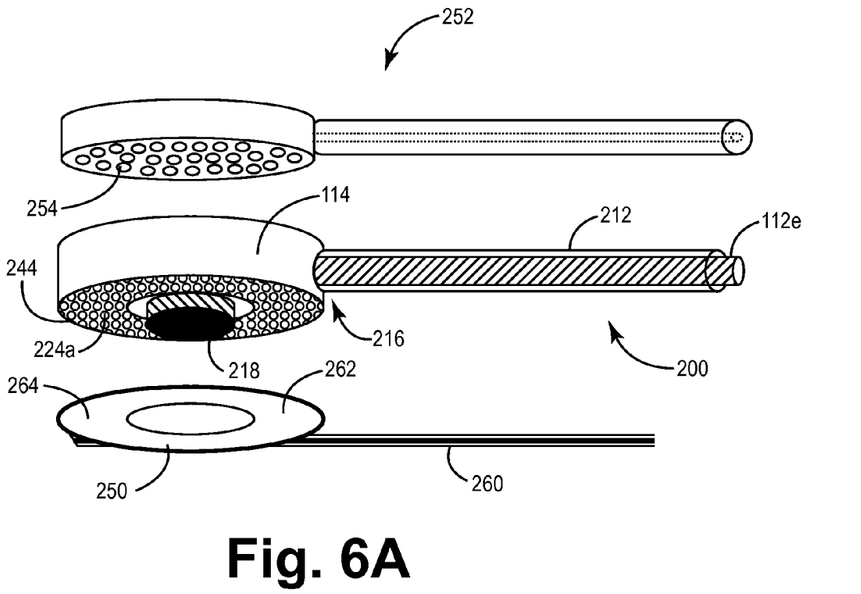
FIG. 6A is a schematic, partial cross-sectional view of a medical electrical lead including a cover and delivery mechanism.

There are numerous ways in which a lead can be delivered and adhered to tissue. Referring to FIG. 6A, lead 200 is depicted as including a cover 250 and a delivery mechanism 252. Bioadhesives can provide strong adhesion to biological matter, often instantly upon contact due to proteins on the tissue site that can react with the bioreactive material 244. The cover 250 can be placed over the bioreactive material 244 to help prevent the bioreactive material 244 from inadvertently bonding to an undesired site (e.g. undesired tissue site, electrode etc.) and/or being deactivated by a body fluid. The illustrated cover 250 preferably comprises an inert material substantially impermeable to body fluids to discourage inadvertent bonding and/or deactivation of the bioreactive layer 244 such that it can no longer be adhered to the desired tissue site. Further, the inert composition helps prevent the cover 250 itself from bonding with tissue during lead delivery. In some embodiments, for example, the cover 250 can comprise a wax paper or a foil.

Figure 6B:
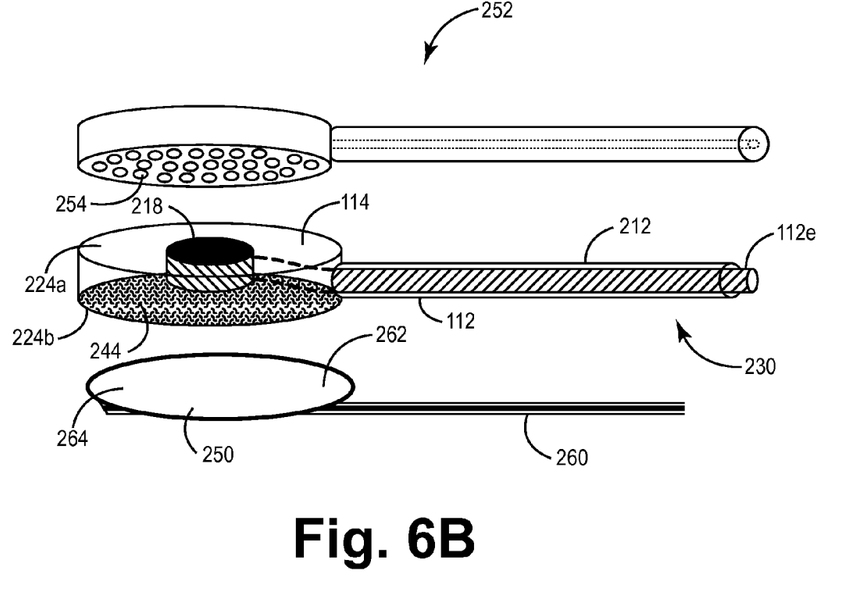
FIG. 6B is a schematic, partial cross-sectional view of a medical electrical lead including a cover and delivery mechanism.

The cover 250 is preferably sealed around and/or on top of the bioreactive layer 244. With respect to FIG. 6A, the cover 250 has an annular shape for covering the similarly-shaped bioreactive layer 244. Referring briefly to FIG. 6B, the cover 250 can take a disk shape, for example, in order to cover the disk-shaped bioreactive layer 244 of FIG. 6B. As is shown, in one or more embodiments, the cover 250 does not cover the electrode 218, in order to facilitate navigation of the electrode to an optimal tissue site.

The bioreactive layer 244 can be substantially sealed between the cover 250 and the first surface 224a by an effective, releasable seal, thus allowing the removal of the cover 250 in order to attach the support member 114 to the tissue site. For example, the cover 250 can be thermally sealed about the bioreactive layer 244, such as, for example, in the case of a cover 250 comprising a wax paper. In other embodiments, the cover 250 can be mechanically sealed against the bioadhesive material. In one or more embodiments, pressure can be used to mechanically seal cover 250 to the bioadhesive material.

Referring again to FIG. 6A, with the bioreactive layer 244 sealed off from the external environment by the cover 250, a physician can move the lead 200 within a body without the bioreactive layer 244 bonding to a tissue site. For example, in the case of an epicardial lead, the physician can move the lead electrode to different positions on the epicardium to locate the preferred tissue site depending on the optimal electrical (mapping) and anatomical properties The physician can then remove the cover 250 and fix or press the support member with the electrode 218 against the epicardium. In preferred embodiments, the physician can then remove the cover 250 proximate the tissue site (e.g., using forceps), thus avoiding the need to remove the lead 200 from the body in order to expose the bioreactive layer 244.

In some cases physicians have located the preferred tissue site using a lead without an attached bioadesive material, removed the lead from the tissue site to apply the off-the-shelf bioadesive material to the lead and/or the tissue site, and then attached the lead to the tissue site. Such a procedure can be managed more easily in a general thoracic surgery in which the heart is exposed than in a limited access procedure such as a thoracoscopy. Leads 200, 230 can facilitate a less invasive implantation compared to conventional passive fixation devices. For example, the support member 114 is small enough in some embodiments to be implanted percutaneously through a small incision or trocar. The cover 250 allows the physician to insert the lead through the small incision and guide it to a tissue site without the bioreactive layer 244 bonding to, for example, a trocar wall or tissue along the route to the tissue site. The physician can then remove the cover 250 proximate the tissue site for attachment.

As FIGS. 6A-6B depict, the delivery mechanism 252 can comprise a vacuum 254 typically, 200-600 pounds per square inch (psi) which can be used to percutaneously position the lead and support member to the preferred tissue site. Other suitable methods of percutaneous delivery can likewise be employed. In some embodiments, the cover 250 is coupled with a tether 260 for removing the cover 250 and exposing the bioreactive layer 244. For example, after guiding the support member 114 to the tissue site, the physician can gently pull the tether to remove the cover 250 and expose the bioreactive layer 244. The physician can then attach the support member 114 to the tissue site with the bioadhesive material. Afterward, the cover 250 and the tether 260 can be removed by pulling the tether out through the incision.

The tether 260 provides an unobtrusive and uncomplicated way to remove the cover 250 without needing to insert and manipulate additional instruments through a limited incision, thus allowing, for example, a smaller incision and/or trocar or thoracoscopy introducer, and potentially less scarring and post-operative pain for the patient. To facilitate removal, the tether 260 can be coupled to the cover 250 in a manner that allows the cover to be removed by simply pulling the tether out through the incision in a direction away from the support member 114. For example, in one embodiment, the cover 250 can comprise a cover proximal portion 262 and a cover distal portion 264. The cover 250 is preferably disposed on the bioreactive layer 244 with the cover proximal portion 262 proximate the lead body distal end 107. In other words, the cover proximal portion 262 is located between the cover distal portion 264 and the lead body distal end 107. The tether 260 can be coupled to the cover distal portion 264. When the tether is pulled away from the support member 114 in a direction along the lead body 212, the cover distal portion 264 is peeled back across the cover proximal portion 262 until the entire cover 250 is removed. The tether 260 and the cover 250 can then be pulled gently through the incision and removed from the body.

Figure 7:
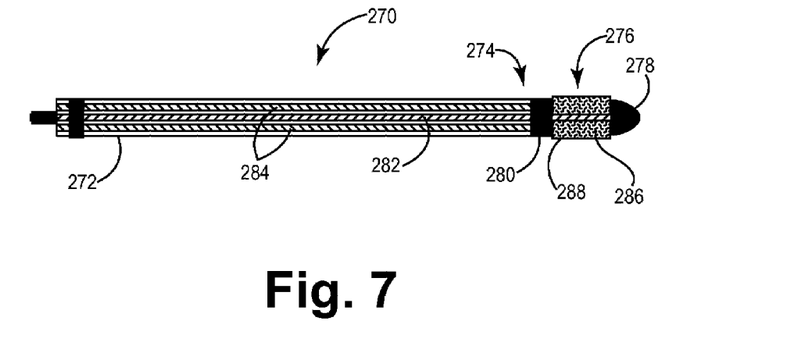
FIG. 7 is a schematic, partial cross-sectional view of a medical endocardial electrical lead.
Figure 8:
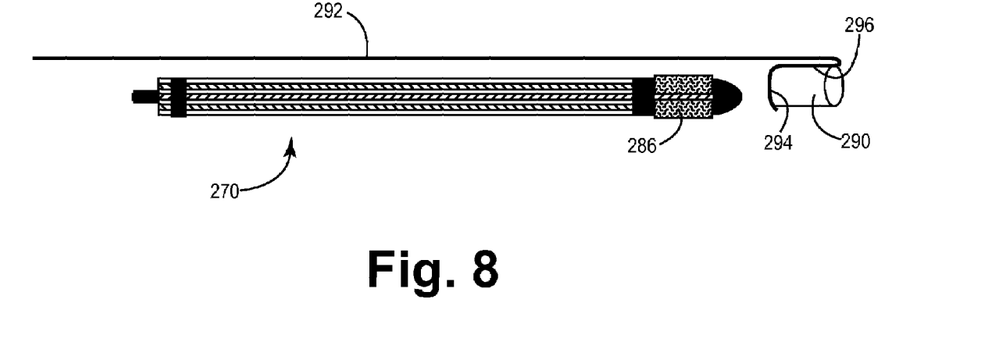
FIG. 8 is a schematic, partial cross-sectional view of a medical electrical lead including a cover.

FIGS. 7 and 8 illustrate perspective, partial cross-sectional views of a medical electrical lead 270. Referring to FIG. 7, the lead 270 is configured as an endocardial lead having a lead body 272 and a lead body distal end 274. The lead body distal end 274 is coupled with a support member 276, which is proximate a tip electrode 278 and a ring electrode 280. The support member 276 comprises a polymeric spacer having a proximal end coupled to the lead body distal end proximate the ring electrode 280, and a distal end coupled to the tip electrode 278. The tip electrode 278 and ring electrode 280 are electrically coupled with respective inner and outer conductor coils 282, 284 disposed within the lead body 272. FIG. 7 further shows a bioreactive material 286 covalently bonded to a rounded first surface 288 of the support member 276. In the embodiment depicted, the bioreactive material 286 is formed as a sleeve sheet on the first surface 288 around the support member 276 between the tip and ring electrodes 278, 280. It will be appreciated, though, that the bioreactive material 286 may be formed in other suitable configurations.

Referring to FIG. 8, the lead 270 can include a cover 290 coupled with a tether 292. In this embodiment, the cover 290 is formed as a cylindrical sleeve that can surround the bioreactive material 286 so that it seals the bioreactive material 286 from its external environment. The cover 290 comprises an inert material to prevent it from bonding with tissue during lead delivery. Further, the cover 290 is substantially impermeable to body fluids (including blood) to help prevent the bioreactive material 286 from deactivating during lead delivery such that it can no longer be adhered to the desired tissue site. In some embodiments, for example, the cover 290 can comprise a wax paper or a foil. To facilitate removal of the cover, the tether 292 is attached at a base 294 of the cover and along a side surface 296 of the cover. As the tether 292 is pulled, the force from the tether rips the cover to free it from around the support member 276.

Lead 270 can be delivered to a predetermined tissue site, for example, within the right atrium or ventricle. Once adjacent the desired tissue site, the tether 292 can be gently pulled to break and to remove the cover 290 and expose the bioreactive material specifically developed for application in the bloodstream/heart 286. The support member 276 can then be fixed to the tissue site and the cover 290 and the tether 292 removed from the body. In an alternate embodiment, the lead is delivered with a steerable catheter which covers and protects the bioreactive material in addition to or in place of the cover 290.

Figure 9:
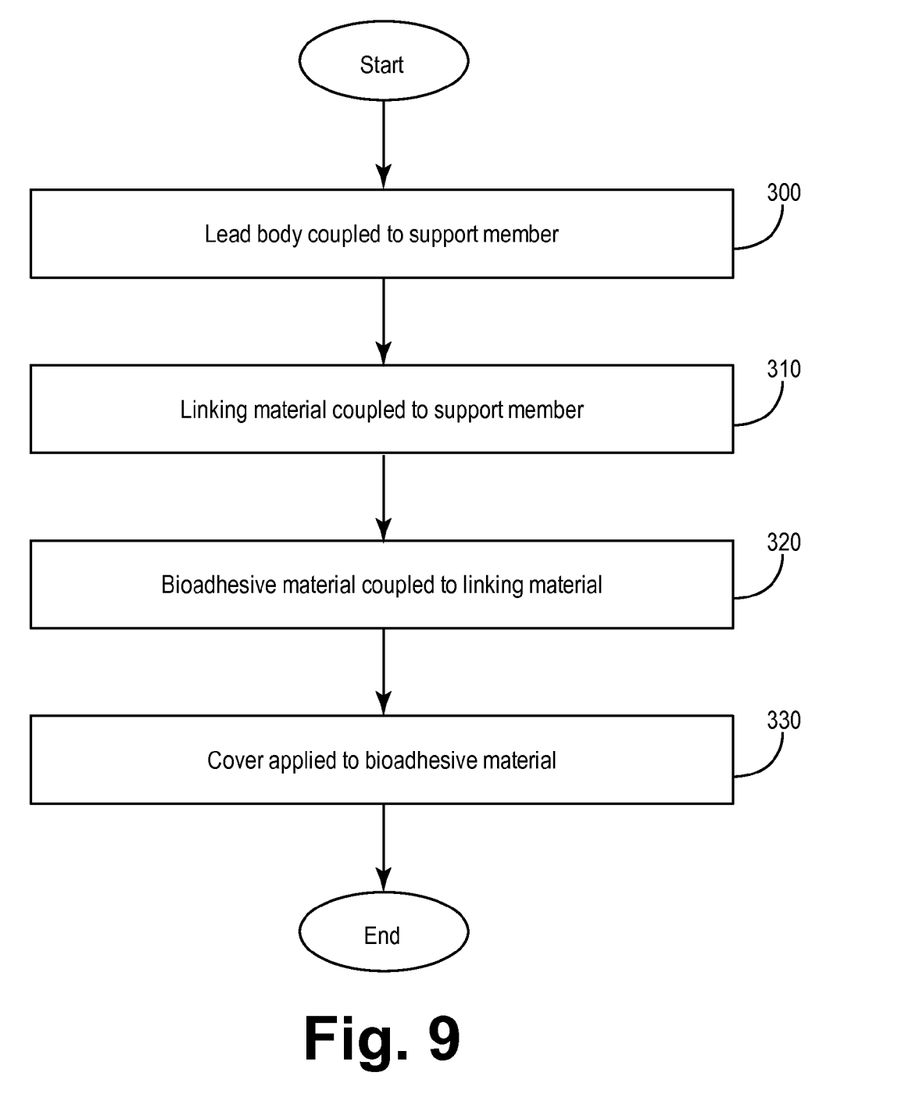
FIG. 9 depicts a flow diagram for forming a passive fixation medical electrical lead.

FIG. 9 depicts a method for forming a passive fixation lead. At block 300, a support member is coupled to a lead body. At block 310, a linking material is coupled to the support member. In one or more embodiments, the linking material is coupled to a first surface of the support member. At block 320, a bioadhesive material is coupled to the linking material. At block 330, a removable cover is applied to the bioadhesive material.

Numerous alternatives exist to the embodiments described herein. For example, although FIG. 5D shows the first surface 224*a* roughened, it is contemplated that an unroughened first surface 224*a* can also be modified by linking material 242. Additionally, the upper surface of the linking material 242 need not follow the roughened contour of the first surface 224*a*. The linking material 242 strengthens the attachment between the bioadhesive material and the first surface 224*a* by covalently bonding the bioreactive material to the first surface 224*a*. For example, the linking material 242 can comprise polyacrylate that is covalently bonded to a first surface 224*a* formed of, for example, polyurethane.

Furthermore, the bioreactive material 244 is not limited to the annular shape depicted, but may be disposed on the first surface 224*a* in a number of suitable shapes and configurations in order to securely attach the support member 114 to a desired tissue site. In addition, one or more electrodes and conductors can be attached to the support member 114 in a variety of locations. As just one example, the support member 114 may have concentric ring and/or tip electrodes with the bioreactive material 244 attached to the first surface 224*a* in between and/or outside the electrodes.

Additionally, as can be seen in FIG. 4, the support member 114 comprises the first surface 224*a* and a second surface 224*b* in which the electrode 218 is proximate the first surface 224*a*, but the bioreactive material 244 is attached to the second surface 224*b* of the support member 114. The different locations of the electrode 218 and the bioreactive material 244 can allow the lead 230 to be attached to a tissue site with the second surface 224*b*, while allowing the electrode 218 to interact with another tissue site. For example, the lead 230 can be placed between the pericardium and epicardium of a heart, with the bioreactive material adhered to the pericardium and the electrode 218 and the first surface 224*a* placed against the epicardium.

Moreover, while one or more embodiments have been described such that the bioreactive adhesion layer 248 is formed over the first surface 224*a* of support member 114, it should be appreciated that the bioreactive adhesion layer 248 can also be formed solely over second surface 224*b*. Additionally, in one or more embodiments, bioreactive adhesion layer 248 can be formed over first and second surfaces 224*a-b*.

Although the present invention has been described in considerable detail with reference to certain disclosed embodiments, the disclosed embodiments are presented for purposes of illustration and not limitation and other embodiments of the invention are possible. It will be appreciated that various changes, adaptations, and modifications may be made without departing from the spirit of the invention and the scope of the appended claims.

What is claimed is:

1. An implantable passive fixation lead comprising:
    an elongate lead body having at least one elongate conductive element, the lead body includes a proximal end and a distal end;
    a polymeric planar support member having a first surface and a second surface, the second surface coupled to the distal end of the lead body;
    a linking material coupled to the first surface of the support member, the linking material comprising a material selected from the group consisting of (3-aminopropyl) trimethoxysilane (APTS), epichlorohydrin (EPC), star PEG-succinimidyl succinate, dextran, and polyacrylic acid and combinations thereof;
    a bioadhesive material coupled to the linking material; and
    a removable cover applied to the reactive adhesive.

2. The implantable medical electrical lead of claim 1, wherein the bioadhesive material comprising one of aldehyde (—CHO), catechol, cyanide (—CN), succimide (—NHS), cyanoacrylate and N-hydroxysuccinimide.

3. The implantable medical electrical lead of claim 2, wherein the cyanoacrylate comprising one of n-butyl cyanoacrylate and 2-octyl cyanoacrylate.

4. An implantable passive fixation lead comprising:
    an elongate lead body having at least one elongate conductive element, the lead body includes a proximal end and a distal end;
    a polymeric planar support member having a first surface and a second surface, the second surface coupled to the distal end of the lead body;
    a linking material coupled to the first surface of the support member;
    a bioadhesive material coupled to the linking material; and
    a removable cover applied to the reactive adhesive.

5. The implantable medical lead of claim 4, wherein the linking material comprises one or more reactive compounds.

6. The implantable medical electrical lead of claim 5, wherein the one or more reactive compounds comprises one of (3-aminopropyl) trimethoxysilane (APTS), epichlorohydrin (EPC), star PEG-succinimidyl succinate, dextran, and polyacrylic acid.

7. The implantable medical electrical lead of claim 4, wherein the bioadhesive material being one of aldehyde (—CHO), catechol, cyanide (—CN), succimide (—NHS) cyanoacrylate and N-hydroxysuccinimide.

8. The implantable medical electrical lead of claim 7, wherein the cyanoacrylate being one of n-butyl cyanoacrylate and 2-octyl cyanoacrylate.

9. The implantable medical electrical lead of claim 4 further comprising a tether coupled to the removable cover.

10. An implantable passive fixation lead comprising:
    an elongate lead body having at least one elongate conductive element, the lead body includes a proximal end and a distal end;
    a polymeric planar support member having a first surface and a second surface, the second surface coupled to the distal end of the lead body;
    a linking material coupled to the first surface of the support member, the linking material comprising at least one of (3-aminopropyl)trimethoxysilane (APTS), epichlorohydrin (EPC), star PEG-succinimidyl succinate, dextran, and polyacrylic acid;
    a bioadhesive material coupled to the linking material; and
    a removable cover applied to the reactive adhesive.

11. An implantable passive fixation lead comprising:

an elongate lead body having at least one elongate conductive element, the lead body includes a proximal end and a distal end;

a polymeric planar support member having a first surface and a second surface, the second surface coupled to the distal end of the lead body;

a linking material coupled to the first surface of the support member, the linking material consisting of a material selected from the group consisting of (3-aminopropyl) trimethoxysilane (APTS), epichlorohydrin (EPC), star PEG-succinimidyl succinate, dextran, and polyacrylic acid and combinations thereof;

a N-hydroxysuccinimide coupled to the linking material; and a removable cover applied to the reactive adhesive.

12. A chronically implantable passive fixation lead comprising:

an elongate lead body having at least one elongate conductive element, the lead body includes a proximal end and a distal end;

a polymeric planar support member having a first surface and a second surface, the second surface coupled to the distal end of the lead body;

a linking material coupled to the first surface of the support member, the linking material consisting of a material selected from the group consisting of (3-aminopropyl) trimethoxysilane (APTS), epichlorohydrin (EPC), star PEG-succinimidyl succinate, and polyacrylic acid and combinations thereof;

a N-hydroxysuccinimide coupled to the linking material; and a removable cover applied to the reactive adhesive.

* * * * *